US00PP13164P2

(12) United States Plant Patent
Cain

(10) Patent No.: US PP13,164 P2
(45) Date of Patent: Nov. 5, 2002

(54) GRAPEVINE CV. 'SUGRATWENTYTHREE'

(75) Inventor: David W. Cain, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 2 days.

(21) Appl. No.: 09/772,099

(22) Filed: Jan. 25, 2001

(65) Prior Publication Data

US 2002/0100087 P1 Jul. 25, 2002

(51) Int. Cl.[7] ..... A01H 5/00

(52) U.S. Cl. ..... Plt./205

(58) Field of Search ..... Plt./205

*Primary Examiner*—Bruce R. Campell
*Assistant Examiner*—Michelle Kizilkaya
(74) *Attorney, Agent, or Firm*—Knobbe, Martens, Olson & Bear

(57) ABSTRACT

A new and distinct grapevine variety characterized by round to ovate seedless black berries that are naturally large, firm, and of high eating quality.

1 Drawing Sheet

BACKGROUND AND SUMMARY OF THE INVENTION

This invention relates to the discovery and asexual propagation of a new variety of grapevine, *Vitis vinifera* cv. 'Sugratwentythree'. The new variety was first hybridized by David W. Cain in Wasco, Kern County, Calif., the variety being originated by controlled hybridization and subsequent ovule culture of normally abortive seeds. The new variety is characterized by producing naturally large black seedless grapes that are responsive to girdling to increase berry size. The high quality, firm berries are round to ovate in shape, and ripen in midseason.

The seed parent is the 'Sun World Breeding Selection 89339-089-291' (nonpatented) variety and the pollen parent is the 'Sun World Breeding Selection 89098-194-167' (nonpatented). The parent varieties were first crossed in May, 1992, with the date of first flowering being May 1995. The new 'Sugratwentythree' variety was first asexually propagated by David W. Cain in December 1995 in Wasco, Kern County, Calif., using hardwood cuttings.

The new grapevine variety cv. 'Sugratwentythree' most nearly resembles its seed parent, 'Sun World Breeding Selection 89339-089-291'. 'Sugratwentythree' differs from its seed parent by having a far superior eating quality. 'Sugratwentythree' produces slightly larger, firmer berries that contain smaller vestigial seed traces, as compared to its maternal parent. The new variety 'Sugratwentythree' differs from its paternal parent, 'Sun World Breeding Selection 89098-194-167' by producing berries that are less prone to cracking and rot. Moreover, 'Sugratwentythree' berries are larger, firmer, and have a later ripening date as compared to the berries of the pollen parent.

The new variety cv. 'Sugratwentythree' distinguished from other commonly grown black grapes such as the 'Ribier' (nonpatented) and the 'Summer Royal' (nonpatented) by several important characteristics.

'Sugratwentythree' resembles the 'Ribier' variety, but differs from it by having small, soft, vestigial seed traces as compared to the lignified, normal-sized seeds present in the 'Ribier' variety. Additionally, berries of the new variety 'Sugratwentythree' are firmer and have a higher sugar content compared to the berries of the 'Ribier' variety.

The new variety cv. 'Sugratwentythree' also resembles the nonpatented 'Summer Royal' grape variety. It is distinguished from this variety by having larger berries (6 to 8 grams per berry as compared to 4.3 to 5.3 grams per berry in the 'Summer Royal' variety). Berries of the 'Sugratwentythree' variety ripen approximately 1 week earlier than the 'Summer Royal' variety, on clusters that are more compact compared to the 'Summer Royal' variety.

The new 'Sugratwentythree' variety has been shown to maintain its distinguishing characteristics through successive asexual propagations by, for example, cuttings.

BRIEF DESCRIPTION OF THE FIGURE

The accompanying drawing in FIG. 1 illustrates in full color a typical cluster of berries, a young shoot, and a mature leaf blade of the new grapevine.

DETAILED BOTANICAL DESCRIPTION OF THE INVENTION

Figure 1:
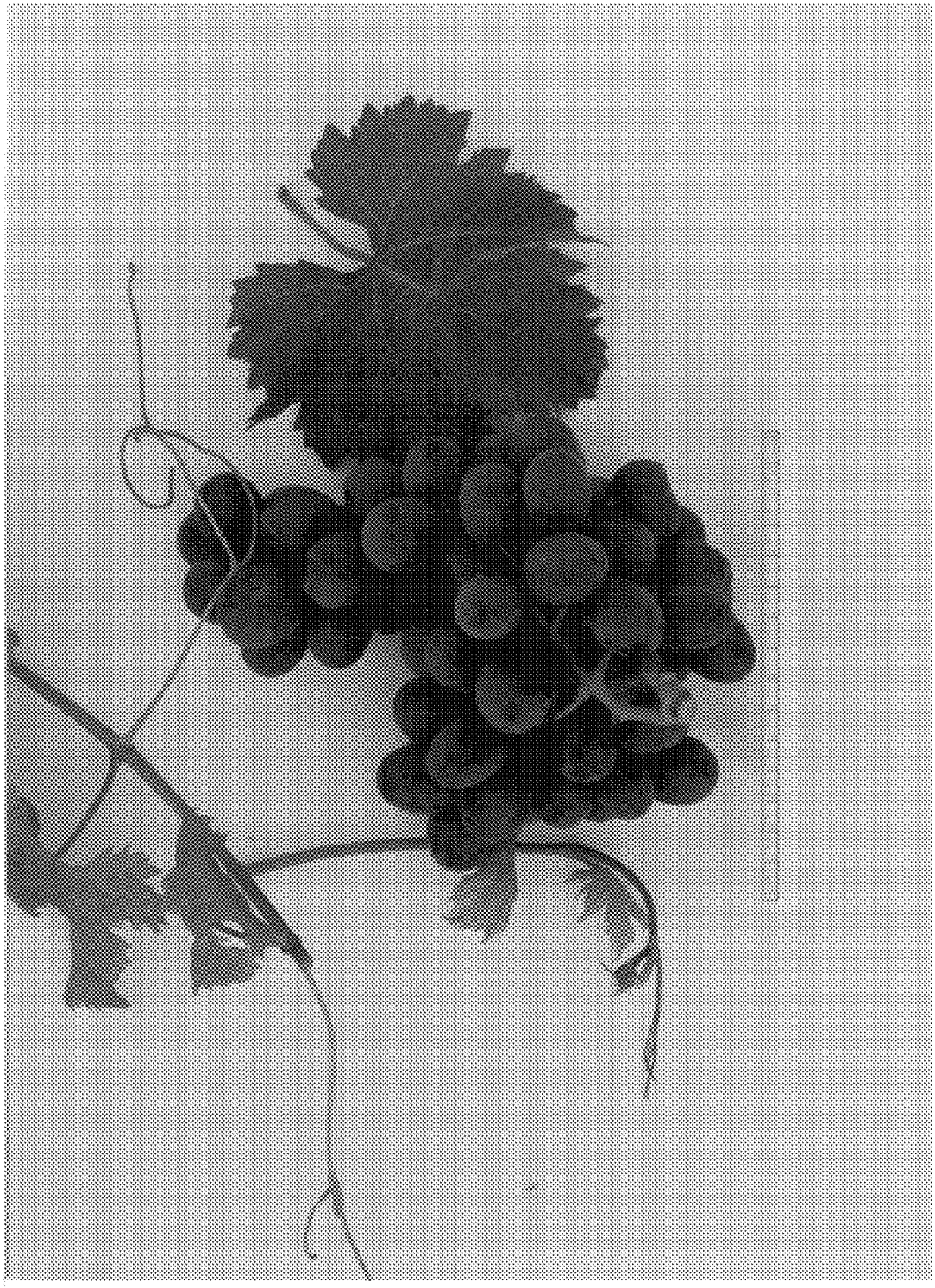

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to 'Sugratwentythree' plants grown in the vicinity of Wasco, Kern County, Calif., during 2000, and is believed to apply to plants of the variety grown under similar conditions of soil and climate elsewhere:

VINE

General:
*Size.*—Large.
*Vigor.*—Vigorous.
*Density of foliage.*—Dense.
*Productivity.*—Medium to low productive.
*Root stock.*—Own.
Trunk:
*Shape.*—Stocky.
*Straps.*—Long, split.
*Surface texture.*—Shaggy.
*Inner bark color.*—About 177B.

SHOOTS

Young shoot:
*Form of tip.*—Fully open.
*Distribution of anthocyanin coloration of tip.*—Piping (striped).
*Intensity of anthocyanin coloration of tip.*—Medium.
*Density of prostrate hairs on tip.*—Medium.
*Density of erect hairs on tip.*—Absent.
Flowering shoot:
*Vigor during flowering.—Medium.*
*Attitude during flowering on shoots which are not tied.*—Horizontal.
*Color of dorsal side of internodes.*—About Green 144A with Red 183B stripes.
*Color of ventral side of internodes.*—About Green 144A.
*Color of dorsal side of nodes.*—About Green 144A with Red 183B stripes.
*Color of ventral side of nodes.*—About Green 144A.
*Density of erect hairs on nodes.*—None.
*Erect hairs on internode.*—Absent.
*Density of prostrate hairs on nodes.*—None.
*Density of prostrate hairs on internodes.*—Absent.
*Anthocyanin coloration of buds.*—Absent.
Tendrils:
*Distribution on the shoot at full flowering.*—Discontinuous.
*Thickness.*—Thick.
*Color.*—Basal area of dorsal side heavily pigmented at approximately Red 183B; ventral side and tips about Green 144B.
*Form.*—Trifurcated.
*Number of consecutive tendrils.*—Up to two.
*Length of tendril.*—Medium, about 22.6 cm.

LEAVES

Young leaves:
*Color of upper surface of first 4 distal unfolded leaves.*—Green to faintly copper.
*Average intensity of anthocyanin coloration of six distal leaves prior to flowering.*—Weak.
*Density of prostrate hairs between veins at lower surface of 4th distal unfolded leaf.*—Absent.
*Density of erect hairs between veins at lower surface of 4th distal unfolded leaf.*—Absent.
*Density of prostrate hairs on veins at lower surface of 4th distal unfolded leaf.*—Medium.
*Density of erect hairs on veins at lower surface of 4th distal unfolded leaf.*—Absent.
Mature leaves:
*Average length.*—About 15.3 cm.
*Average width.*—About 19.4 cm.
*Size of blade.*—Large.
*Shape of blade.*—Pentagonal.
*Number of lobes.*—5.
*Anthocyanin coloration of main veins on the upper side of the blade.*—Absent.
*Mature leaf profile.*—Undulate.
*Blistering surface of blade upper surface.*—Strong.
*Leaf blade tip.*—In the plane of the leaf.
*Undulation of margin.*—Pronounced.
*Apex.*—Cuspidate.
*Thickness.*—Medium.
*Undulation of blade between main and lateral veins.*—Overall.
*Shape of teeth.*—Both sides straight.
*Length of teeth.*—Medium.
*Ratio length/width of teeth.*—Small.
*General shape of petiole sinus.*—Lobes slightly overlapping.
*Tooth at petiole sinus.*—Present.
*Petiole sinus limited by veins.*—Absent.
*Shape of upper lateral sinus.*—Lobes slightly overlapping.
*Depth of upper lateral sinus.*—Medium.
*Density of prostrate hairs between veins on lower surface of blade.*—Absent.
*Density of erect hairs between veins on lower surface of blade.*—Absent.
*Density of prostrate hairs on main veins on lower surface of blade.*—Sparse.
*Density of erect hairs on main veins on lower surface of blade.*—Sparse.
*Density of prostrate hairs on main veins on upper surface of blade.*—Absent.
*Autumn coloration of leaves.*—About Yellow 11B (typically, frost kills leaves before extensive color change, as leaves change color very late in the season).
Upper surface:
*Color.*—About 137A to 137B.
*Surface texture.*—Rugose.
*Surface appearance.*—Semi-glossy.
*Goffering of blade.*—Present.
Lower surface:
*Color.*—About 137D.
*Anthocyanin coloration of main veins on lower leaf surface.*—Absent.
*Glossiness.*—Weak.
*Pubescence.*—Absent.
*Surface texture.*—Rugose.
Petiole:
*Length of petiole.*—Short.
*Length of petiole compared to middle vein.*—Much shorter.
*Density of prostrate hairs on petiole.*—None.
*Density of erect hairs on petiole.*—None.
*Shape of base of petiole sinus.*—V-shaped.
Woody shoot:
*Shape.*—Stocky.
*Internode length.*—Medium, about 125 mm.
*Width at node.*—About 12.6 mm.
*Cross section.*—Circular.
*Surface.*—Striate.
*Main color.*—About Reddish-Brown 176A.
*Lenticels.*—Absent.
*Density of erect hairs on nodes.*—None.
*Density of erect hairs on internodes.*—None.
*Growth of axillary shoots.*—Medium, about 29.5 cm.

Buds:

*Shape.*—Slightly pointed.

*Size.*—Medium, about 0.52 cm length by 0.61 cm width.

*Position.*—Slightly held out.

*Cane bud fruitfulness.*—Basal fruitful.

*Time of bud burst.*—Medium.

FLOWERS

General:

*Flower sex.*—Hermaphrodite.

*Length of first inflorescence.*—Short, about 13.0 cm.

*Position of first flowering node.*—$3^{rd}$ to $4^{th}$.

*Number of inflorescences per shoot.*—Up to 1.

*Date of full bloom.*—May 6, 2000.

*Time of bloom.*—Medium, as compared with similar varieties in the growing area of Wasco, Kern County, Calif.

*Size* (*diameter of fully open flower*).—Medium.

FRUIT

General:

*Ripening period.*—Medium, about 12 days after 'Thompson Seedless' variety.

*Use.*—Fresh market.

*Keeping quality.*—Good.

*Resistance.*—Insects: Medium. Diseases: Medium.

*Shipping quality.*—Good.

*Date of first harvest.*—Aug. 10, 2000.

*Solids-sugar.*—Medium (~18%).

*Refractometer test.*—About 17.0° brix.

Cluster:

*Bunch size* (*peduncle excluded*).—Medium.

*Bunch length* (*peduncle excluded*).—Intermediate, about 14.3 cm.

*Bunch width.*—About 14.1 cm.

*Bunch weight.*—Medium, averaging about 498 grams.

*Bunch density.*—Dense.

*Number of berries.*—About 86.

*Form.*—Conical.

Peduncle:

*Length of peduncle.*—Short, about 4.1 cm.

*Lignification of peduncle.*—Medium.

*Color.*—About 145B.

Berry:

*Size.*—Large.

*Uniformity of size.*—Variable.

*Berry weight.*—High, about 7.33 g/berry.

*Shape.*—Round to ovate.

*Presence of seeds.*—Rudimentary, about 0.44 mg/seed.

*Cross section.*—Circular.

*Dimensions.*—About 23.9 mm longitudinal by 22.1 mm horizontal axis.

*Skin color* (*without bloom*).—About Blue-Black 202A.

*Coloration of flesh.*—None.

*Juiciness of flesh.*—Slightly juicy.

*Berry firmness.*—Firm.

*Particular flavor.*—None.

*Bloom* (*cuticular wax*).—Strong.

*Pedicel length.*—Long, about 8.5 mm.

*Berry separation from pedicel.*—Difficult.

*Visibility of hilum.*—Unclear.

Skin:

*Thickness.*—Medium.

*Texture.*—Medium.

*Reticulation.*—Absent.

*Roughness.*—Absent.

*Tenacity.*—Tenacious to flesh.

*Tendency to crack.*—None.

Sugratwentythree: Table of R.H.S. Color Codes:

| | | | R.H.S. Color Chart |
|---|---|---|---|
| VINE: | Trunk: | Inner bark color: | 177B |
| SHOOTS: | Flowering Shoot: | Dorsal side of internodes: | 144A with 183B stripes |
| | | Ventral side of internodes: | 144A |
| | | Dorsal side of nodes: | 144A with 183B stripes |
| | | Ventral side of nodes: | 144A |
| | Tendrils: | Basal area of dorsal side: | 183B |
| | | Ventral side and tips: | 144B |
| LEAVES: | Mature Leaves: | Autmn coloration of leaves: | 11B |
| | Upper Surface: | | 137A to 137B |
| | Lower Surface: | | 137D |
| | Woody Shoot: | | 176A |
| FRUIT: | Peduncle | | 145B |
| | Berry: | Skin color (without bloom): | 202A |

What is claimed is:

1. A new and distinct variety of grapevine cv. 'Sugratwentythree' as herein illustrated and described.

* * * * *